United States Patent [19]

Allen et al.

[11] Patent Number: 4,712,460
[45] Date of Patent: Dec. 15, 1987

[54] INTEGRATED DRUG DOSAGE FORM AND METERING SYSTEM

[75] Inventors: Jimmy D. Allen, Los Altos; Michael E. Cobb, San Jose; Robert S. Hillman, Cupertino; Dennis R. Mungall, Redwood City; Vladimir E. Ostoich, San Jose; Gary H. Stroy, Los Altos, all of Calif.

[73] Assignee: Biotrack, Inc., Mt. View, Calif.

[21] Appl. No.: 798,780

[22] Filed: Nov. 18, 1985

[51] Int. Cl.⁴ .............................................. B65D 83/00
[52] U.S. Cl. ....................................... 83/208; 83/648; 83/649; 424/443; 604/57
[58] Field of Search ................. 83/202, 203, 204, 205, 83/648, 649, 167; 424/27; 604/59, 57

[56] References Cited

U.S. PATENT DOCUMENTS

| | | | |
|---|---|---|---|
| 3,361,021 | 1/1968 | Toth | 83/649 X |
| 3,494,235 | 2/1970 | Postolowski | 83/649 X |
| 3,760,669 | 9/1973 | Rosenthal | 83/208 X |
| 4,325,277 | 4/1982 | Uchida et al. | 83/648 X |
| 4,457,195 | 7/1984 | Brooks | 83/649 X |
| 4,608,894 | 9/1986 | Lee | 83/649 X |

*Primary Examiner*—Donald R. Schran
*Attorney, Agent, or Firm*—Bertram I. Rowland

[57] ABSTRACT

An automatic drug tape dispensing and metering device and a roll of drug tape housed in a small portable dispenser unit. The dispenser contains a measurement device for carefully measuring the length of tape as it is dispensed from the dispenser. A counter monitors the remaining doses of drug tape remaining within the dispenser. A timer device may be provided to alert the patient that it is time for the medicament to be dispensed. As the lid of the dispenser unit is opened, the measured length of drug tape is severed from the roll by a cutter blade incorporated into the lid. The device permits a physician to accurately customize the dosage and administration of the medicament to be givne a patient by adjusting the tape length released for each single dose and selecting the time intervals between dosages.

25 Claims, 4 Drawing Figures

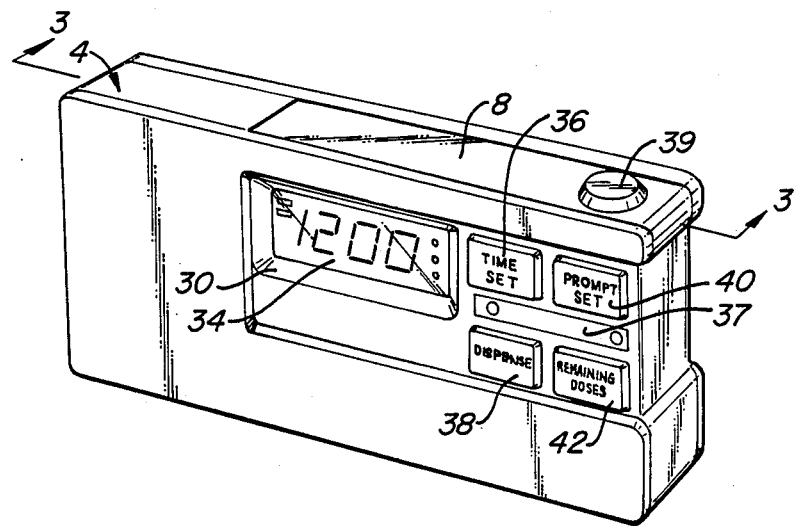
FIG._1.
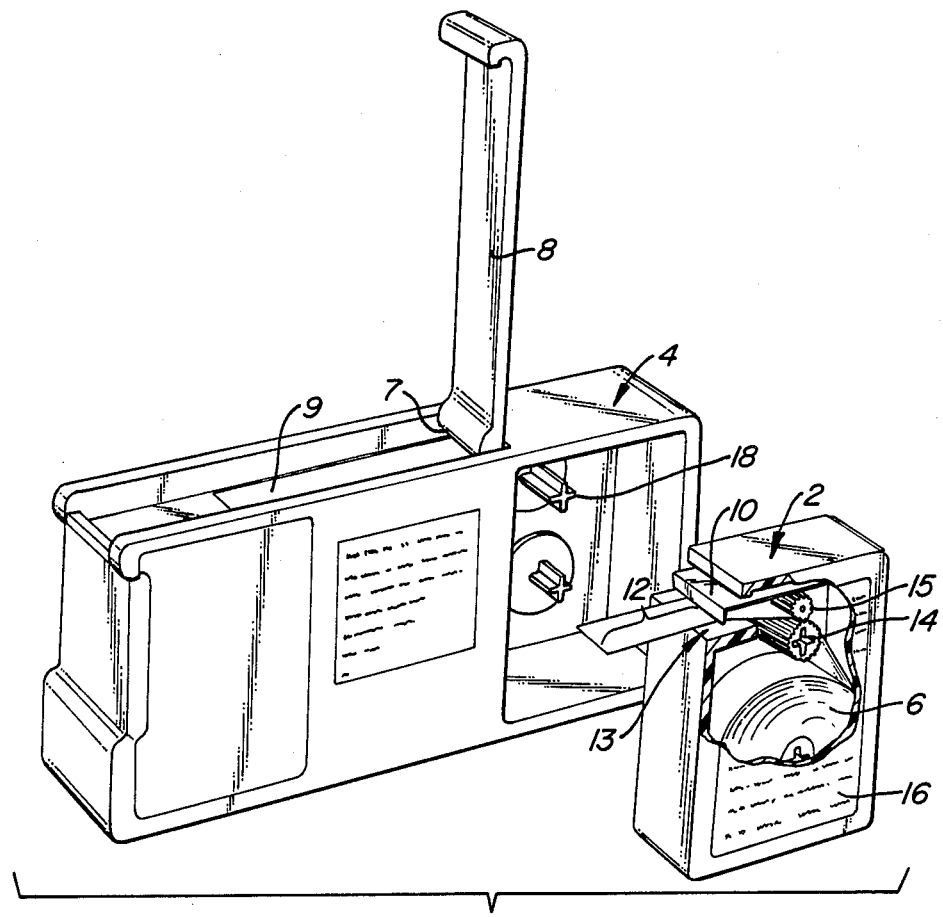
FIG._2.

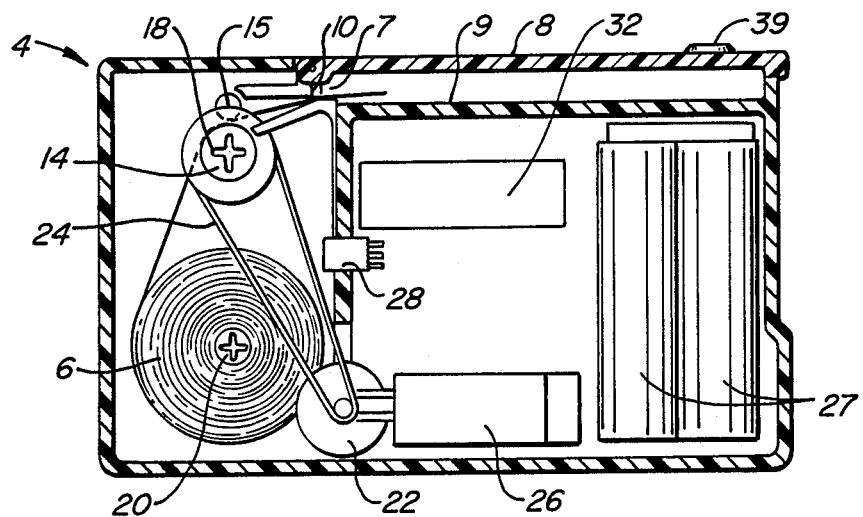
FIG._3.
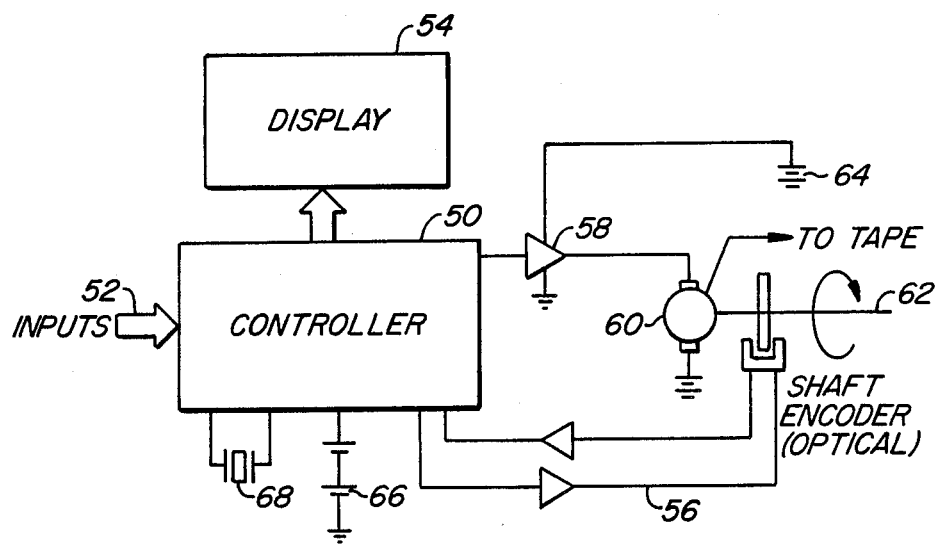
FIG._4.

INTEGRATED DRUG DOSAGE FORM AND METERING SYSTEM

BACKGROUND OF THE INVENTION

A number of medicaments that are presently administered orally must be prescribed to patients in dosages which are tailored to the mass, age and medical history of the patient. Medications in pill or capsule form are limited by the discrete dosages of the particular tablet or capsule size. Pills may sometimes be scored along their diameter to provide roughly half the dosage when broken along the score line. However, this rough method is inaccurate and inadequate other than for half-dosages. By way of example, sodium warfarin requires personalized dosing to achieve the desired therapeutic effect and to avoid undesirable side effects such as bleeding. Available multi-potency tablets usually require unconventional, confusing dosing patterns to achieve the appropriate therapeutic response.

Some medicaments lend themselves to a liquid form which is somewhat more adaptable in dosage. However, liquids are less convenient and require the patient to be responsible for measurement of the dosages. Although liquid medicaments are theoretically infinitely meterable, in practice, the dosages commonly used are rough and inaccurate. Liquids are somewhat less portable and often require refrigeration.

Accuracy in the treatment of a patient undergoing a drug therapy regimen also requires the patient to take the appropriate dosage over an extended period of time at appropriate intervals. Some treatments require a uniform dosage over uniform intervals of time, while other medicaments require "tapered dosages" which may increase, level off and decrease over the treatment period. An easily varied dosage regimen which encourages patient compliance with the regimen is greatly needed. None of these treatment regimens are easily accomplished using tablets, capsules or liquid medicaments.

SUMMARY OF THE INVENTION

A drug dispensing system is provided having a continuous drug containing tape which can be provided in a dispensing device, which automatically dispenses programmed dosages. The tape is formulated to have a controlled amount of drug per unit length, with the tape length dispensed being organoleptically acceptable to the user and the formulation providing the proper dissolution rate upon ingestion. The dispenser can be equipped with various control devices to automatically dispense the proper drug dosage at predetermined time intervals, monitor the number of dosages dispensed and alert the user to the time for taking the medicament.

These and other features of the invention will become more apparent by reference to the accompanying drawings.

BRIEF DESCRIPTION OF THE DRAWINGS

FIG. 1 is a perspective illustration of the dispenser unit.

FIG. 2 is an exploded perspective view of the tape cassette and the dispenser with a cutaway view of the cassette.

FIG. 3 is a cross-sectional view taken from line 3—3 in FIG. 1 of the dispenser unit with the cassette unit in place.

FIG. 4 is a schematic block diagram of the control unit of the dispenser.

DETAILED DESCRIPTION OF THE INVENTION

The subject invention is the combination of a continuous medium for providing a predetermined drug dosage in tape form in an organoleptically and physiologically active form for oral ingestion and a convenient dispensing device adapted for metering the tape in accordance with a predetermined regimen. The tape is formulated to ensure physical, chemical and physiological stability and can be housed in the dispensing device.

The dispensing device lends itself to use with any medicaments in a continuous, uniform tape form, particularly the tapes of the subject invention. The drug tape is of the type to be administered to patients orally. The dispenser combines the convenience of pill-form drugs with the adaptability of liquid-form drugs, permitting completely personalized dosing regimens.

The dosage of the drug along the length of the tape may be uniform, or continuously varying. A single drug may be incorporated into the tape or a mixture of more than one drug. For example, in a birth control formulation of the drug tape, the concentrations of two hormones such as estrogen and progestrone could be varied. These drug concentrations would be incorporated into the tape during its manufacture.

The dispenser is a small, portable automatic drug metering device for the recurring, accurate dispensing of a drug tape. The drug tape is stored in a roll mounted within a disposable cassette unit which fits into the dispenser housing. The cassette unit and dispenser housing form a case to enclose and protect the drug tape from contamination, and to provide for the easy refilling of the dispenser unit. The dispenser housing contains a drive mechanism for unrolling the drug tape, a measurement means for metering the length of drug tape dispensed and a cutter for severing a length of drug tape from the roll.

The dispenser may also include a timer, an audible alarm and a display for indicating the time intervals at which the drug tape will be dispensed, and the dosage for which the dispenser has been set. The timer may be directly linked to the drive mechanism such that the drug tape is automatically dispensed, or, alternatively, linked to the audible alarm such that the patient is prompted to activate the dispenser at the appropriate time. A message displayed on an LCD display could also remind the patient that it is time to dispense the medication. The timer may also permit the user to actuate the dispensing mechanism only over a selected period of time between the preselected time intervals, with the dispensing mechanism inoperable, "locking out" the patient from dispensing the drug at all other times. A counter may be provided which reminds the patient of the number of dosages remaining to be dispensed with a memory device which keeps a record of the administration of the drug tape.

The tape form provides the combined advantages of liquid and solid form drugs. It is a convenient and portable form which is meterable through its length. The dispenser device provides the storage means for the drug, as well as providing for the accurate measurement of the tape. The time feature assures that the patient is reminded to administer the drug. Child safety is improved, since safety features incorporated into the dispenser make inadvertent activation of the dispenser very difficult.

A physician can prescribe a customized dosage of the medicament. This dosage is preset to correspond to a length of tape corresponding to the appropriate discrete dosage to be administered to the patient. This single dosage length is automatically dispensed in the dispenser so that the patient automatically withdraws the appropriate length. An ample supply of the tape can be stored within a small dispenser case. The physician can also select the time intervals at which the drug should be ingested by the patient, and a pharmicist sets the in accordance with the timer prescription timer to activate the alarm or to automatically dispense the drug tape at the end of these time intervals. The dispenser also monitors and displays the number of dosages dispensed so that the patient may be made aware of the need to obtain a refill of the prescription. A record of the administration of the drug tape may also be stored in a memory and displayed on the display of the dispenser.

Varying dosages can be accomplished by alerting the patient to have the single dosage length reset by the physician or pharmacist, or by permitting the patient to reset the single dosage length at the appropriate times or by programming the variable dose into memory.

To prevent the unauthorized or accidental dispensing of the medicament, the device may also be provided with a lock mechanism or the mechanism may only be activated at the preprogrammed time intervals.

The cassette unit containing the drug tape is disposable and inexpensive. The dispenser housing portion of the device incorporates the more costly elements of the invention and could be reusable.

The dispenser case is easy and inexpensive to fabricate and portable in size. It may be constructed so as to be either disposable or refillable with disposable cassettes. Operation of the dispenser must be simple, so that minimal instruction is necessary and it can be readily employed by elderly patients. It must be uncomplicated and as automatic as possible to encourage patient compliance with the prescribed dosing regimen.

The dispenser device is illustrated in perspective in FIGS. 1 and 2. In this embodiment of the invention, the dispenser device is an enclosed case comprising a disposable tape cassette 2 and a reusable dispenser unit 4. The supply of drug tape is stored as a roll 6 within the cassette 2. Housing 4 includes a hinged cover 8 which includes an actuating cam 7 that depresses a cutting blade 10 which severs the single dose length 12 as cover 8 is opened. The exterior face of cassette 2 contains a location for a prescription label 16 identifying the contents of the cassette and the usual prescription information.

The disposable cassette unit 2 containing the drug tape roll 6 may be sealed once the roll of drug tape is in place to prevent contamination. The access opening 13 through which the tape feeds may be covered temporarily with adhesive tape or foil. To install cassette 2 into dispenser unit 4, the pharmacist removes the temporary cover of the access opening and slides the cassette 2 into dispenser 4 so that the drive capstan 18 meshes with capstan hub 14.

The dispenser device is automated to assure that the patient accurately dispenses the appropriate dosage of drug tape at the preselected time intervals. Cassette unit 2 provides a disposable, easily replaced cartridge to be used with reusable dispenser housing 4. Cassette unit 2 snap fits into dispenser housing 4 and further provides an enclosure to protect the roll of drug tape roll 6 from contamination.

The drug tape is unrolled from the supply and carefully measured from cassette unit 2 by a motorized drive mechanism. The terminal end of the drug tape is fed to a tray 9 located beneath the hinged cover 8. As the patient lifts hinged cover 8, a cutting blade 10 at the hinge joint severs the tape from roll 6. Tapes may also be designed that have a memory so as to coil into a capsule.

The apparatus for the measurement and dispensing of the drug tape is further shown in conjunction with FIG. 3. Pinch roller 15 of cassette unit 2 frictionally engages with corresponding capstan hub 14 which meshes with capstan 18 within dispenser housing 4. Capstan 18 is driven by a belt 24 which is rotated by gears 22 which are powered by a small motor/encoder 26. Post 20 supports the roll and is mounted so as to freely rotate. Batteries 27 to power the motor 26 fit within the transverse portion of the dispenser unit opposite the drug tape cassette. Roller 15 frictionally engages and drives the drug tape without slippage to assure accurate measurement of the drug tape when motor 26 is activated.

To pre-set the single dosage lengths of the drug tape, the pharmacist or patient activates a switch to the appropriate setting. Such a switch, accessible only by exposing the interior portion of the dispenser unit, is shown as pharmacist set switch 28, which is used in customizing the unit for dosage and time intervals between each dispensing of the drug tape dosages. Such limited accessibility of the set switch prevents the patient from inadvertently resetting the dosage. The microswitch programs the controller of the motor/encoder 26 with the appropriate number of rotations of the motor shaft corresponding to the preselected length of drug tape to be dispensed.

FIG. 1 illustrates one possible switching arrangement for the invention. Display panel 30 and the various function buttons disposed on the front face of the dispenser unit can be seen in FIG. 1. The single display window 34 displays the current time, the times at which the drug tape should be dispensed, the remaining number of doses, the dosage value, and the administration record of the cassette. A blinking light in the display window may be provided to indicate a low battery. Four switches and a set bar are shown and are provided to control these various functions.

Although the control mechanism may be designed to customize the dispenser for use with a particular drug dispensing regimen, the embodiment illustrated herein represents a typical design. It is to be understood that more specialized applications involving nonuniform dosage drug tapes, irregular time intervals or tapered dosages are within the scope of the present invention. The particular embodiment illustrated herein relates to one form of a dispenser that would be used in prescribing a uniform dosage drug tape over regular time intervals.

The several switches disposed along one face of the dispenser housing control the various functions of the device. An LCD display is incorporated into the same face of the housing at a display panel 30.

Time set switch 36 may be used to set the clock for the dispenser timer. The same time set switch 36 may be used in combination with set bar switch 37 to adjust the clock timer.

Dispenser switch 38 may be used to display the dosage of the drug at which the dispenser has been set. In order for the device to actually dispense the drug tape, cover switch 39 provided along hinged cover 8 must be pressed simultaneously with dispenser switch 38. This dual switching requirement provides for an additional locking safety feature to prevent inadvertent or unauthorized activation of the device.

Prompt set switch 40 may be used to sequentially display the various times at which the dispenser has been set to dispense the drug. The same prompt set switch 40, when used in conjunction with pharmacist set switch 28 (see FIG. 3), accessible only from the interior of the dispenser, may be used to program, or "set" the various times at which the drug is to be dispensed.

Remaining dose switch 42 may be used to display the number of doses of drug tape remining in the cassette. When used in conjunction with set bar switch 37, the initial number of doses of drug tape available in the cassette can be set by the pharmacist or patient.

FIG. 4 is a schematic block diagram of the control system of the dispenser unit. The controller 50, e.g. a state machine, in the preferred embodiment is a programmed microprocessor unit. The function switch signals are shown as the input signals 52 to the controller. The function switches of the apparatus (time set switch 36, time set bar 37, dispense switch 38, dose dispense switch 39, prompt set switch 40 and remaining dose switch 42 shown in FIG. 1) for providing the input signals 52 are disposed along the exterior surface of the front wall of the dispenser housing, as is the display, (display 34 shown in FIG. 1) designated in FIG. 4 by numeral 54.

Tape feed and measurement means are provided by shaft encoder buffers 56, motor 60 and shaft 62. A battery 64 provides a power source for the motor, while a backup battery 66 protects the memory of the controller 50. A crystal 68 provides for the timing input to the controller.

The controller 50 provides for a preset dosage signal corresponding to the single dosage length to the shaft encoder buffers 56 to control the rotations of shaft 62 to determine the length of tape dispensed. The dosage signal is provided to the display 54 when dispense switch 38 is depressed to display the dosage.

The crystal 68 provides the clock functions to the controller 50. The preselected time interval over which the drug is to be dispensed is provided to the controller by prompt set switch 40 pressed simultaneously with set bar 37. The controller can then provide a time signal at the end of each time interval to either provide an audible alarm (not shown) which prompts the patient to dispense the drug tape, or to the motor driver 58, to automatically actuate the motor.

A counter (not shown) may be coordinately linked to the feed mechanism and the controller. Each time a single dosage length is dispensed, a count signal is provided to the counter to increment and display either the number of doses dispensed or the number of doses remaining to be dispensed. Either the number of doses dispensed or the number of doses remaining to be dispensed is displayed in response to an input signal 52. If desired, the total number of doses to be dispensed may be preselected via remaining dose switch 42 simultaneously pressed with set bar 37. Alternatively, the counter could be linked only to the gear means to act independently of the controller.

The controller may be further provided with a memory to store the times and dosages for each time a single dosage length is dispensed. The memory would be operably connected to the dispense switch 38 and the controller 50 to record the times at which each single dosage length is dispensed. The dosage signal could be also linked to the memory such that the dosages could be stored in conjunction with the times of dispensing the drug tape. This would be of importance in instances where tapered dosages are used.

The drug tape may be prepared by any convenient means, such as casting, extruding and pressing. Illustrative of the conditions for preparing the tape are the conditions employed for casting. Add the polymer to $\frac{1}{3}$–$\frac{1}{2}$ of the total volume of water to be added, with the water at 75°–85° C., and allow 5–20 min to wet out completely. The total water will be about 80–85% of the aqueous polymer mixture. Agitate for 5–20 min at a slow but sufficient rate to prevent settling. Add the remaining water at 5°–15° C. and allow mixture to cool to room temperature. The remaining components are added and agitated to homogeneity. The mixture may then be spread onto a flat nonstick surface with a Gardner knife and allowed to dry under ambient conditions to provide a uniform sheet having about 0.5 the initial wet thickness. A sample is then calibrated for drug level.

Depending upon the method of preparing the drug tape, the formulation may have to be varied to accommodate the temperature requirements, particularly thermal stability, solubility, or the like. The width of the tape will be a convenient one, ranging from about 0.25 to 1 cm, preferably about 0.35 to 0.75 cm, more preferably about 0.5 cm. The thickness will be governed by a variety of considerations, such as mechanical stability, dissolution rate, ease of oral ingestion, amount of drug per unit length, and the like. Thicknesses may vary from 2 mil to 20 mil.

The formulations which are employed must fulfill certain mechanical and physical requirements to be stably and reliably metered in the dispensing device. The tape should have a tensile strength of at least about 250 psi, preferably at least about 300 psi, more preferably in the range of about 500 to 2000 psi (at approx. 1 lb load), with a % elongation of less than about 100, preferably less than about 50, (measured on an Instron Universal Testing Machine).

The tape should undergo equal to or less than 5%, usually less than 2%, preferably less than about 1%, dimensional change due to ambient changes in temperature and humidity. The tape must be nonblocking. That is, under usual ambient conditions the tape may be rolled on itself and stored as a roll, but will not stick to itself and is readily dispensed.

The formulation should be able to accommodate about 0.01 to 5 $mg/mm^3$ of drug, usually in the form of a powder, where the error in the amount of drug dispensed should not exceed 10%, usually less than about 5%, preferably less than about 3%. With this drug load the dispensed tape should be capable of acting in an analogous manner to a tablet, as to the ability to be swallowed and the rate of dissolution. The drug may be a micronized powder, a liquid, or other form which is readily dispersible.

The basic substance will be a physiologically acceptable polymer, as the base, particularly polyvinylpyrrolidone or hydroxypropylcellulose. The polymer content will range from about 10 to 20 weight % of the formulation, preferably 10 to 15 weight %, more preferably 11.5 to 13 weight %. A physiologically acceptable extender or filler is employed as the major ingredient, conveniently a polysaccharide such as maltodextrin or starch, which may be derived from any natural source, e.g. corn, potato, etc., and may be as isolated or further processed, e.g. enzymatically partially hydrolyzed. The extender will be present in at least about 30 and not more than 50 weight %, usually about 32 to 45 weight %, preferably about 35 to 40 weight %.

Some plasticizer will be employed. The plasticizer which is employed will depend to some degree on the manner in which the tape is formed. The plasticizer should have a high enough boiling point so as not to evaporate during processing and be compatible—disperse uniformly—with the polymer. Plasticizers which may be employed include 1,2-propylene glycol, glycerine, triethyl citrate, etc., with triethyl citrate being the plasticizer of choice for high temperature production of the tape, e.g. hot melt extrusion. One or more plasticizers may be used to advantage. The total amount of plasticizer will be at least 5 weight % and not more than 40 weight %, usually at least about 10 weight %, and less than about 20 weight %, usually less than about 15 weight %.

Optionally, the next significant ingredient may be a humectant, which serves to enhance the rate of disintegration and dissolution of the tape upon ingestion, which will be present in from 0 to 20 weight %. Conveniently, sorbitol provides humectant qualities, while also being a sweetner. The sorbitol may be present and when present will be in at least about 5 weight % and less than about 20 weight %, usually about 10 to 15 weight %. To further aid dissolution, disintegrants may be employed, e.g. croscaramellose Na type A, in amounts not to exceed about 10 weight %.

The remaining ingredient will be the drug, which will usually be at least about 1 weight % of the tape and less than 50 weight %, usually less than about 35 weight %.

Other minor ingredients may be added for organoleptic qualities, such as for flavor, coloring, texture, etc., for storage stability, such as antioxidants, UV absorbers, bacteriostats, bacteriocides, etc. These components are individually present in less than 1 weight %, usually less than 0.5 weight %, and greater than about 0.001 weight %.

After the tape is formed it may be further processed. The surface may be coated by painting or spraying, a message may be imprinted in the tape, the tape may be scored to enhance the ease and accuracy of dispensing and the like.

In order to demonstrate the properties of tapes made with the subject formulations, a number of tapes were prepared with warfarin as the drug at about 25 weight %. The tape composition is preferably prepared by mixing the polymer and drug as a first batch (3 min) in a sigma-type mixer, followed by the addition of the plasticizer, where the polymer and drug become dispensed in the plasticizer. To the plasticized mixture, heated to about 50°-70° C., particularly 60° C., is then added a prepared mixture of the other ingredients: starch, humectant, minor additives, and the heating continued until a temperature of about 100°-150° C., particularly 130° C. is reached (9 min). The mixture is then pressed at 130° C. to a thickness of 8-9 mils. The films were tested using an Instron Universal Testing Machine for tensile strength and elongation. Blocking of films was tested by placing two films together under a wire screen and subjecting them to 4-5 hr exposure to temperatures of 100° F. and 140° F. and humidities of atmospheric laboratory conditions, 50% and 80%. Tests were performed in a Tinnius Olsen temperature and humidity testing machine.

The following tables indicate the results:

| Ingredients | FORMULATION (Wt %) | | | |
|---|---|---|---|---|
| | 1 | 2 | 3 | 4 |
| HPMC[1] | 16.86 | 16.86 | 16.86 | 12.29 |
| Plasticizer[2] | | | | |
| 1,2-PG | 11.25 | 4.22 | 7.73 | |
| TEC | | | | 12.29 |
| Starch[3] | 37.30 | 37.30 | 37.30 | 37.30 |
| Sorbitol | 9.50 | 16.54 | 13.02 | 13.02 |
| Warfarin | 25.00 | 25.00 | 25.00 | 25.00 |
| Red color | 0.09 | 0.09 | 0.09 | 0.09 |

[1]HPMC — hydroxypropylmethylcellulose USP-Exp. polymer XD 1214
[2]1,2-PG — 1,2-propylene glycol TEC — triethyl citrate - Citroflex (Pfizer)
[3]Sta-Rx - A.E. Staley Mfg. Co.

TENSILE STRENGTH TESTS

| Sample No. | Width (in) | Thickness (in) | Area Sq. in | Load (lb) | Tensile (psi) | Machine Travel (in) | % Elongation |
|---|---|---|---|---|---|---|---|
| 1a* | 0.250 | 0.0104 | 0.0026 | 0.83 | 319 | 1.945 | 97 |
| " | " | 0.0105 | 0.0026 | 0.75 | 285,302 | 1.888 | 94,96 |
| 1b° | " | 0.0106 | 0.00265 | 0.91 | 343 | 1.81 | 91 |
| " | " | 0.010 | 0.0025 | 0.71 | 316 | 2.055 | 103 |
| " | " | 0.0096 | 0.0024 | 0.76 | 317,325 | 1.85 | 93 |
| 2 | " | 0.011 | 0.00275 | 3.0 | 1091 | 0.15 | 7.5 |
| " | " | 0.0085 | 0.0021 | 1.75 | 833,962 | 0.25 | 10,8.8 |
| 3 | " | 0.0105 | 0.00263 | 0.7 | 266 | 0.91 | 45.5 |
| " | " | 0.0103 | 0.00258 | 0.58 | 225,246 | 1.043 | 53.2, 49.4 | a* - pressed at 120° C.
b° - pressed at 140° C.

Samples 1 and 2 were tested for blocking: (a) 100° F., 50% humidity, 5 hr; (b) 100° F., 80% humidity, 5.5 hr. Slight and no blocking was observed for 1 and 2 with the former conditions. Some blocking with easy separation for both tapes with the latter conditions.

In the final test, dissolution rate was determined at room temperature in deionized water with a stirrer speed of approximately 150 rpm. A relatively linear dissolution rate was observed with substantially complete dissolution at about 3 min, while a coumadin tablet was approximately linear to 50% dissolution over 4 min, and completely dissolved in 5 min.

A cassette containing approximately one meter of tape would provide about a one month supply to the patient. This cassette could fit into a dispenser unit roughly the size of a cigarette package.

The subject invention provides a convenient accurate method for automatically dispensing accurate amounts of a drug for ingestion. The tape and dispenser are coordinated to provide a stable tape able to be dispensed from a roll and a dispenser which is capable of automatically metering out a predetermined length of tape which determines the amount of drug. An organoleptically and physiologically acceptable tape has been devised for use in the dispenser.

The foregoing is a complete description of the invention, but is not intended to limit the scope of the invention, except as stated in the appended claims. While the above provides a full and complete disclosure of the preferred embodiments of the invention, various modifications, alternative constructions and equivalents may be employed without departing from the true spirit and scope of the invention.

What is claimed is:

1. A drug tape dispenser for adjustably dispensing preselected single dosage lengths of drug tape from a drug tape supply, comprising:
   a portable housing having a dispenser site and a cassette receptacle site;
   a cassette adapted for removably engaging the housing at the cassette receptacle site;
   drive means in the housing at the cassette receptacle site;
   feed means disposed in said cassette to receive and engage the drug tape from the drug tape supply when the feed means is operably engaged by said drive means when said cassette engages the housing at the cassette receptacle site;
   a first discharge site in said housing located to introduce said tape into said dispenser site;
   a second discharge site located in said cassette so as to mate with the first discharge site when said cassette engages the housing at the cassette receptacle site;
   a controller coordinately actuating the drive means for automatically measuring a single dosage length of drug tape; and
   a cutter disposed proximate to the first discharge site to sever the single dosage length from the supply of drug tape.

2. The dispenser of claim 1, further comprising a counter operably connected to the feed means for counting the number of single dosage lengths dispensed.

3. The dispenser of claim 1, wherein the feed means comprises a pair of capstans disposed to receive and engage the drug tape from a drug tape roll, wherein one of the capstans is operatively engaged by said driving means.

4. The dispenser of claim 1, wherein the controller comprises a state machine.

5. The device of claim 1, wherein the controller comprises a clock.

6. The dispenser of claim 1, wherein the feed means further comprises a manual actuator linked to the feed means to be actuated by the user.

7. The dispenser of claim 3, wherein the dispenser further comprises dual actuation means wherein the controller provides that the feed means may only be actuated when a first manual actuation means linked to the feed means is actuated by the user and a second actuation means is actuated by the controller.

8. The dispenser of claim 1, wherein the controller is linked to a clock for actuating the second actuation means for a preset time period between preselected time intervals.

9. The dispenser of claim 1, wherein the dispenser further comprises:
   a first display, functionally responsive to the controller and designating the number of remaining doses and the dosage length.

10. The dispenser of claim 1, wherein the case further comprises a tray proximate the discharge site for receiving the severed single dosage length of drug tape.

11. The dispenser of claim 10, wherein the case further comprises a hinged cover disposed to cover the tray.

12. The dispenser of claim 11, wherein the cutter is a blade disposed along the hinged edge of the cover such that as the cover is opened, the drug tape is severed.

13. The dispenser of claim 1, wherein the controller further comprises
   a clock located in the case for measuring time intervals over which the drug tape is to be dispensed, the clock further providing a time signal generated at the end of a preselected time interval; and
   a second display responsive to the time signals to display the times at which the drug is to be dispensed.

14. The dispenser of claim 13, wherein the controller actuates the feed means in response to the time signal.

15. The dispenser of claim 13, wherein the clock further comprises an alarm which is actuated by the time signal.

16. The dispenser of claim 13, wherein the controller further comprises a memory recording the time to provide a dispense signal.

17. The dispenser of claim 16, wherein the second display designates an administration record of the times at which a single dosage length was dispensed in response to the administration signals.

18. A housing having enclosing walls comprising one element of a drug metering device for the accurate, recurring dispensing of medicaments in a continuous drug tape form in adjustable, preselected single dosage lengths, where the drug tape is provided in a cassette having a first discharge site and a mounting to support the drug tape, wherein the housing and the cassette fit together to form an enclosed case, said housing comprising:
   a second discharge site, a dispenser site and a cassette receptacle receiving site in the housing adapted for sealed engagement with the cassette whereby the first discharge site mates with the second discharge site;
   gear means in the housing situated for drivably engaging the mounting of the cassette to feed the drug tape from the cassette through the first and second discharge sites to the dispenser site;
   controller means in the housing coordinately actuating the gear means for automatically measuring the single dosage lengths of drug tape;
   a display on a wall of the housing, regulated by the controller for displaying the number of remaining doses and the dosage corresponding to the single dosage length; and
   a cutter disposed proximate the dispenser site for severing the drug tape.

19. The housing of claim 18, wherein the housing further comprises a tray proximate the dispenser site for receiving the severed single dosage length of drug tape.

20. The housing of claim 19, wherein the housing further comprises a hinged cover disposed to enclose the tray and having the cutter provided at the hinged edge such that as the cover is opened to expose the tray, the drug tape is severed to provide a single dosage length of drug tape.

21. The housing of claim 18, wherein the dispenser further comprises a clock operatively connected to the gear means and the controller, for actuating the gear means and controller to automatically dispense a single dosage length of drug tape at the end of a preselected time interval.

22. The housing of claim 18, further comprising a counter for counting the number of single dosage lengths of drug tape that have been dispensed, said counter being actuated by the controller.

23. A drug metering device for the recurring, accurate dispensing of medicaments in a continuous drug tape form in adjustable, preselected single dosage lengths, having an enclosed case comprising:

a portable housing having a front wall, a rear wall, a cassette receptable site accessible through the rear wall, a first discharge site, and a dispenser site;

a cassette for containing a supply of the drug tape, adapted for sealed engagement with the housing at the cassette receptacle site, having a shaft for supporting the drug tape, and having a second discharge site which mates with the first discharge site;

gear means in the housing for frictionally engaging the shaft in the cassette, the gear means controlling the feed of the drug tape from the cassette through the first and second discharge sites to the dispenser site;

a counter in the housing, operably connected to the gear means for counting the number of single dosage lengths that are dispensed;

drive means in the housing, coordinately actuating the gear means and the counter, for automatically driving the gear means to feed the single dosage length of drug tape to the dispenser site;

a clock in the housing for measuring time intervals over which the drug tape is to be dispensed;

a controller in the housing, operably connected to the drive means and the clock;

a display on the front wall of the housing, communicating with the controller to display the number of remaining doses, the dosage and the times at which the drug is to be dispensed; and a cutter disposed proximate to the dispenser site for severing single dosage lengths of drug tape from the supply of drug tape.

24. A drug dispensing system comprising:
(a) a drug dispenser comprising:
a housing for a drug tape roll;
means for feeding said tape from said roll; and
means for cutting preselected lengths from said roll in tape receiving relationship with said roll; and
(b) a drug tape roll housed in said housing characterized by being capable of being fed from a roll and cut at preselected lengths providing a predetermined medicament dosage, having a tensile strength of at least about 250 psi, a thickness of from about 2 to 20 mil, from about 0.01 to 2 mg drug/mm$^3$ and less than about a 5% dimensional change due to ambient variations in temperature and humidity.

25. A drug dispensing system, comprising:
(a) a portable drug dispenser comprising:
a housing capable of containing a drug tape roll;
means for feeding said tape from said roll; and
means for cutting preselected lengths from said roll, said means for cutting being located in tape-receiving relationship with said roll; and
(b) a drug tape roll housed in said housing characterized by being capable of being fed from said roll and cut at preselected lengths to provide a predetermined medicament dosage.

* * * * *